United States Patent
Wang

(10) Patent No.: US 7,410,459 B2
(45) Date of Patent: *Aug. 12, 2008

(54) CARDIAC SUPPORT DEVICE AND METHOD

(76) Inventor: Dai-Yuan Wang, 6406 Woodland Rd., Bethesda, MD (US) 30817

( * ) Notice: Subject to any disclaimer, the term of this patent is extended or adjusted under 35 U.S.C. 154(b) by 484 days.

This patent is subject to a terminal disclaimer.

(21) Appl. No.: 10/333,147

(22) PCT Filed: Jul. 18, 2001

(86) PCT No.: PCT/US01/22553

§ 371 (c)(1),
(2), (4) Date: Jan. 15, 2003

(87) PCT Pub. No.: WO02/05871

PCT Pub. Date: Jan. 24, 2002

(65) Prior Publication Data

US 2003/0208098 A1 Nov. 6, 2003

Related U.S. Application Data

(63) Continuation of application No. 09/618,236, filed on Jul. 18, 2000, now Pat. No. 6,454,697.

(51) Int. Cl.
*A61N 1/362* (2006.01)
*A61N 5/04* (2006.01)

(52) U.S. Cl. .................. 600/17; 600/509; 604/6.11; 604/6.14

(58) Field of Classification Search ............... 604/4.01, 604/6.11, 6.13, 6.14, 500, 506; 600/16–18, 600/508, 509, 521
See application file for complete search history.

(56) References Cited

U.S. PATENT DOCUMENTS 2,553,247 A 5/1951 Fowler (Continued)

FOREIGN PATENT DOCUMENTS

CN 1444493 9/2003

(Continued)

OTHER PUBLICATIONS

International Preliminary Examination Report, for Wang, Dai-Yuan, Int'l App'l No. PCT/US01/22553, Filed on Jul. 18, 2001, Dated Sep. 17, 2002.

(Continued)

*Primary Examiner*—Mark W Bockelman
(74) *Attorney, Agent, or Firm*—Law Offices of Albert Wai-Kit Chan, PLLC

(57) ABSTRACT

The invention relates to a cardiopulmonary bypass pump that can be used with medication to put the heart into asystole or near asystolic status. The patent describes equipment used in conjunction with medication to temporarily replace the function of the heart and to allow the heart to survive with minimal oxygen supply for hours or days, and for the heart to recover from ischemic or other insult or other damage without being subjected to a heavy working load. The invention provides a means to stop blood flow to the heart for a relatively long period of time, thereby allowing the performance of certain procedures that require coronary artery blockade. It also allows the heart to stop contracting, which may result in safer and easier performance of some procedures. A medication is given to the patient while the device is in use in order to stop the heart or slow the heart rate to a minimal level to decrease cardiac oxygen requirements without significant hemostasis in the pulmonary circulation.

16 Claims, 2 Drawing Sheets

U.S. PATENT DOCUMENTS

| | | | |
|---|---|---|---|
| 4,034,742 A | | 7/1977 | Thoma |
| 4,231,354 A | | 11/1980 | Kurtz et al. |
| 4,334,180 A | | 6/1982 | Bramm et al. |
| 4,540,399 A | | 9/1985 | Litzie et al. .................... 607/4 |
| 4,599,093 A | | 7/1986 | Steg, Jr. |
| 5,011,469 A | * | 4/1991 | Buckberg et al. .......... 604/6.11 |
| 5,069,661 A | * | 12/1991 | Trudell ...................... 604/6.14 |
| 5,526,810 A | | 6/1996 | Wang |
| 5,647,350 A | | 7/1997 | Mutch et al. ........... 128/204.21 |
| 5,674,452 A | * | 10/1997 | Carson et al. ................. 422/46 |
| 5,722,930 A | | 3/1998 | Larso, Jr. et al. ............. 600/16 |
| 5,879,316 A | | 3/1999 | Safar et al. ..................... 604/4 |
| 5,941,841 A | | 8/1999 | Mutch et al. .................... 604/4 |
| 6,019,722 A | | 2/2000 | Spence et al. ............... 600/210 |
| 6,087,394 A | * | 7/2000 | Duhaylongsod ............. 514/478 |
| 6,296,630 B1 | | 10/2001 | Altman et al. .............. 604/508 |
| 6,454,697 B1 | * | 9/2002 | Wang .......................... 600/17 |
| 6,458,323 B1 | * | 10/2002 | Boekstegers ................. 422/44 |

FOREIGN PATENT DOCUMENTS

| | | |
|---|---|---|
| EP | 0309642 A | 4/1989 |
| EP | 1 303 333 | 4/2003 |
| WO | WO 87/02894 | 5/1987 |
| WO | PCT/US01/22553 | 7/2001 |

OTHER PUBLICATIONS

European Search Report for Dai-Yuan Wang, European Application No. 0184216.0, Filed Feb. 17, 2003, Dated Nov. 20, 2006.

Takano, et al., "Successful Treatment of Profound Left Ventricular Failure by Automatic Left Ventricular Assist System", World Journal of Surgery, vol. 9, pp. 78-88 (1985).

U.S. Office Action for Dai-Yuan Wang, U.S. Appl. No. 09/618,236, filed Jul. 18, 2000, dated Apr. 2, 2002.

U.S. Notice of Allowance and Fees Due for Dai-Yuan Wang, U.S. Appl. No. 09/618,236, filed Jul. 18, 2000, dated Jun. 4, 2002.

U.S. Issue Notification for Dai-Yuan Wang, U.S. Appl. No. 09/618,236, filed Jul. 18, 2000, dated Sep. 5, 2002.

European Communication for Dai-Yuan Wang, European Application No. 0184216.0, Filed Feb. 17, 2003, Dated Apr. 26, 2007.

European Office Communication for Dai-Yuan Wang, European App'l No. 01984216.0, filed Feb. 17, 2003, Dated Apr. 26, 2007.

European Office Communication for Dai-Yuan Wang, European App'l No. 01984216.0, filed Feb. 17, 2003, Dated Jan. 22, 2008.

International Search Report for Dai-Yuan Wang, International App'l No. PCT/US2001/022553, filed Jul. 18, 2001, Dated Feb. 13, 2002.

\* cited by examiner

CARDIAC SUPPORT DEVICE AND METHOD

The invention disclosed herein claims priority of PCT Application No. PCT/US01/22553, filed Jul. 18, 2001, claiming priority of U.S. Ser. No. 09/618,236, filed on Jul. 18, 2000, the contents of which are incorporated by reference here into this application. Throughout this invention, various references are cited. Disclosures of these publications in their entireties hereby incorporated by reference into this application to describe more fully the state of the art to which this invention pertains.

TECHNICAL FIELD

It is well known that if the blood supply to the heart is significantly compromised and the demand of the heart for blood supply remains unchanged or increases (so called supply demand mismatch), the muscle of the heart will be reversibly damaged in a few minutes to a few hours, depending on the severity of the mismatch and other factors. This time limit of the survival of the heart in this condition—only minutes to hours—presents a major challenge to physicians and exposes patients to high mortality and morbidity during myocardial infarction heart attack). Patients may not be able to survive the heart attack or, if they do, they may develop severe heart failure due to extensive injury to the heart. This imposes a huge social and financial burden on society.

In most situations, blood supply to the heart can not be improved immediately and, if the demand of the heart for blood supply can be decreased significantly, the heat may survive this insult much longer pending further treatment and may gain enough time to recover from the insult. This is conventionally accomplished in part by keeping the patient at rest, including the use of sedatives if necessary. Also, the patient is typically given supplemental oxygen to make enhanced use of the available cardiovascular function.

The heart works as a pump to maintain blood circulation. The function of circulation is to maintain blood pressure at a certain level to provide perfusion to the organs of the body. Ali the prior art inventions available to artificially support circulation are designed as left ventricular supportive devices with an assumption that the heart will continue to play a central role in maintaining blood circulation. They are designed to assist the heart when it can not work normally such as a left ventricular assistant device. Alternatively considering coordination between the heart and the system, such as the cardiac-pulmonary bypass machine, which also requires a complicated procedure.

BACKGROUND ART

Previous inventions were designed to provide cardiac-pulmonary bypass as an assistance to the heart and allow the heart to work continuously even there is significant compromise of blood supply to the heart, or to replace the function of the heart when it fails to function. For example, U.S. Pat. No. 4,540,399 to Litzie discloses a cardiopulmonary bypass machine. It allows a physician to control the speed of the pump to maintain blood pressure at a certain level. U.S. Pat. No. 5,879,316 to Safar also discloses a cardiopulmonary bypass machine, which provides differential perfusion of different organs including the heart. It considers selective perfusion of the heart as a part of resuscitation and allows the heart to stop for one to two hours. However, it requires a complicated procedure.

A design of a pump was made public (Tokano H. et. al, *World J. Surgery* 9:78-88, 1985), which has EKG gating and left arterial pressure feed back to control work load on the heart. The left arterial pressure is used to determine the work load on the heart and, therefore, to control pump activity for unloading volume from the left ventricle. It is also a left ventricular assistant device and allows the heart to continue to contract and to assume a central role in circulation.

A number of inventions have disclosed cardiopulmonary bypass machines for open-heart surgery. They require insertions of a catheter into the heart chambers and the great blood vessels surgically and extensive technical support.

If a machine can maintain blood pressure, a physician can put the heart into asystole, or near asystole, without significant compromise to the function of the organs. Patients can survive without the heart's functioning, and the heart survives until a definitive treatment takes place. The heart has enough time to recover from a transient myocardial insult.

DISCLOSURE OF THE INVENTION

The invention relates to a cardiac support system which can be used in conjunction with medication to render the heart in an asystolic or nearly asystolic status. It is a goal of the invention that the work load of the heart is minimized by coordination between the activities of the heart and of the system during induction and maintenance of the asystolic or nearly asystolic status and later the resumption of the normal activity of the heart.

Because the invention allows a physician to put an acutely diseased heart into an asystolic or nearly asystolic status, the physician has enough time to perform further diagnostic tests and therapeutic intervention, and to transfer the patient to a referral center for further treatment. The invention is designed with the concept that the heart needs to stop working if its blood supply is significantly compromised. It is also a consideration of the invention that the pump system disclosed herein is easy to use by most medical practitioners in most medical facilities throughout the world.

No previous invention has been designed with the concept of intentionally rendering the heart temporarily asystolic or nearly so in order to allow adequate time for the performance of diagnostic tests, therapeutic maneuvers, and recovery from the myocardial insult. To achieve this goal, the device and the heart need precisely coordinated activity. This may be achieved by a complex interaction between the electromechanical activity of the heart and the device. None of the prior art devices teaches adequate mechanisms for coordination between the heart and pump activity. It is important to have mechanisms of coordination between the cardiopulmonary pump and the heart when attempting purposeful induction and maintenance of an asystolic or nearly asystolic status.

For example, '399 does not take it into account that the heart needs to stop working. Neither '399 nor '316 teach intentional cessation of the heart as a primary treatment instead of as a resuscitation attempt or as a part of open heart surgery. Neither patent has a mechanism to sufficiently coordinate the contraction of the heart with the activity of the cardiopulmonary bypass machine, such as EKG gated pump activity with interaction between pressure control and EKG gating, although some of them did have EKG gated activity and pressure feedback. Although there are EKG gating and pressure control (only left atrial pressure feed back) devices known in the art, there is no interaction among EKG, arterial pressure, and contraction of the heart and pump activity.

The invention provides a method of facilitating cardiac rest in a human comprising induction of a controlled asystolic state in the human and application of life support techniques while the human is in the asystolic state.

Typically, the induction includes administration of a medication or medications such as calcium channel blockers, beta adrengenic blockers, antiarrhythmics and potassium. These drugs are well known in the art. Examples of calcium channel blockers include verapamil and diltiazem. Examples of beta adrenergic blockers (or beta adrenergic receptor antagonists) include propranolol, esmolol and bretylium. Examples of antiarrhythmic agents include lidocaine, adenosine, procainamide and quinidine.

Some of the medications can be placed in more than one category. For instance, the beta blockers can be useful as antiarrhythmic agents. If potassium is used to slow or to stop the heart, intravenous potassium chloride is a preferred embodiment. For this purpose, the potassium is administered in a large vein or a central vein, such as the femoral, jugular or subclavian vein. Other drugs may be administered as is well known in the art. For example, pain killers and sedatives may be indicated. Examples include morphine, phenobarbital and diazepam.

Life support techniques of the invention include application of a closed extra-corporeal circulation system. Such a system typically includes a venous conduit, a gas exchanger, a pump for pumping at least a portion of the patient's blood, and an arterial conduit. Preferably, the artificial circulation system is arranged such that the venous conduit is connected to a vein of the patient, the arterial conduit is connected to an artery of the patient, the gas exchanger is connected to at least one of the venous conduit and the arterial conduit, and the pump is connected to at least one of the venous conduit and the arterial conduit. Usually the gas exchanger is adapted both to remove at least a portion of a quantity of carbon dioxide from the patient's blood and to add a quantity of oxygen to the patient's blood. A heat exchanger may be included, and it is connected with any two of the group comprising the arterial conduit, the pump, the gas exchanger, and the venous conduit. Preferably, the pump included in the circulation system is a pulsatile pump.

The closed system preferably includes an EKG gating mechanism that has an EKG sensor means for sensing the human's heartbeat, and a feedback means for coordinating the EKG sensor means with the pump wherein the pump discontinues for a time of at least one heartbeat sensed by the EKG sensor means and resumes pumping when the heartbeat is not sensed by the EKG sensor means at a rate or at a volume which is needed to maintain blood pressure above a preset level and is controlled by an intrinsic rate or volume setting.

The closed system may include an arterial pressure sensor that has a feedback means for coordinating the arterial pressure of the human with the pumping of the pump such that the pump changes at least one of pumping rate and pumping volume when the pressure sensor senses a pressure different from a predetermined arterial pressure range. The pressure sensor is also used to re-initiate the pump activity after EKG gating means stops the pumping activity as described herein and when the blood pressure sensor senses a fall in blood pressure.

The pump increases a volume output of the pump by changing at least one of pump rate and pump volume when the pressure sensor senses an arterial pressure less than the predetermined arterial pressure and decreases a pumping rate when the pressure sensor senses an arterial pressure higher than the predetermined arterial pressure.

The closed system includes a gating coordination means for coordinating the EKG sensor means with the arterial pressure sensor means. To promote adequate arterial blood pressure in the human, the pressure sensor means is adapted to override the EKG gating means to control the pump for at least one of pumping rate and pumping volume.

The pump preferably includes at least two chambers. The two chambered pump is coordinated such that one of the chambers is receiving blood into itself while the other of the chambers is emptying blood from itself. The closed system further includes a QRS reset mechanism that is adapted to sense a QRS complex generated by the patient and to reset the pump's pumping when the QRS complex is sensed by the reset mechanism. In this embodiment, the resetting of the pumping is accomplished such that the chamber that was receiving blood before the reset will resume receiving blood until a predetermined volume is received, and such that the chamber emptying blood will resume emptying blood until a predetermined volume is emptied.

The invention further provides a method of facilitating cardiac rest in a patient comprising induction of a state of either reversible bradycardia or reversible asystole in conjunction with the application of life support techniques. Bradycardia can refer to a heart rate of from 1 to 60 beats per minute. Alternatively, bradycardia can refer to a heart rate of from 1 to 10 beats per minute.

Additionally, the invention provides a method of facilitating cardiac rest in a patient who has sustained a cardiac insult comprising induction of a controlled state of lowered metabolism of the myocardium of the human. This state includes decreased heart rate and decreased oxygen utilization. During this time, life support techniques are administrated including extra-corporeal circulation through a closed system. The closed system has a pump, a gas exchanger, a heat exchanger, and a systolic gating mechanism. The controlled state of lowered metabolism facilitates further treatment to the heart without injury to the heart or compromise of blood supply the other vital organs.

The gas exchanger is typically adapted to remove CO2 from and to add 02 to at least a portion of a volume of blood pumped through the closed system. Also, the gas exchanger is usually located in series between a vein of the human and the pump.

Preferably, the systolic gating mechanism is adapted to coordinate the pump and systole such that the pump is restrained from pumping during systole. The gating mechanism preferably includes a pressure sensor and a feedback means to the pump. The feedback means is adapted to control at least one of pumping rate and cardiac volume output. Typically, at least one of the pumping rate and the volume output is sufficient to maintain a predetermined pressure.

Other features and advantages of the invention will be apparent from the following description of the preferred embodiments thereof, and from the claims. Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

BEST MODE FOR CARRYING OUT THE INVENTION

Figure 1:
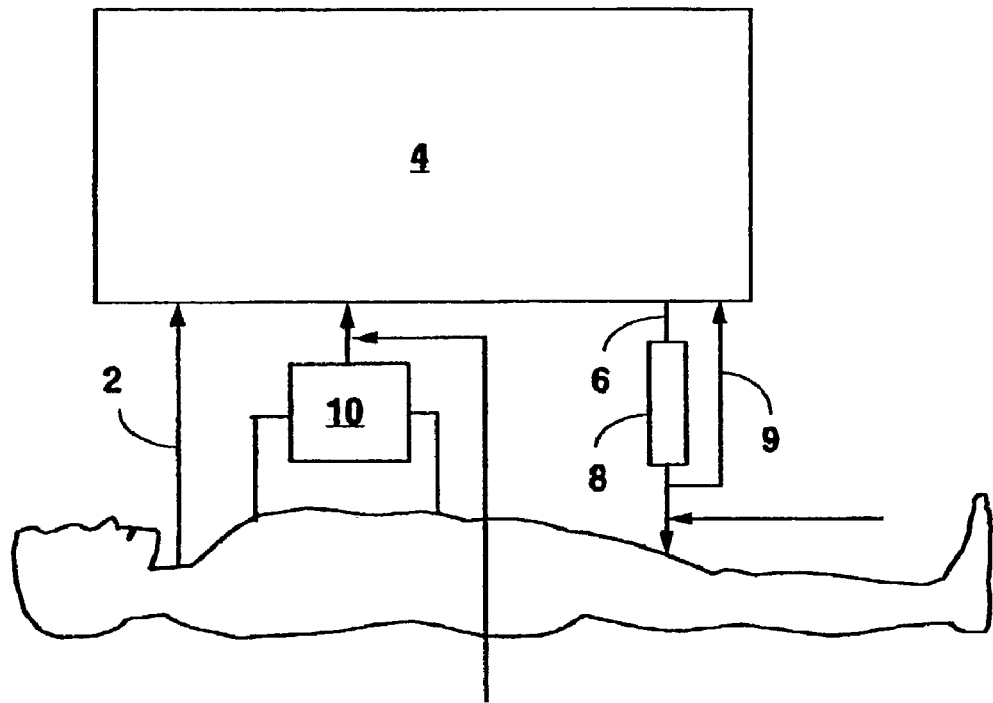
FIG. 1 is a diagram of an embodiment of the pump system.

The system includes a pump which drains the blood from the veins and pumps the blood back to the arteries of a patient. Typically the patient is a human, but the invention encompasses veterinary applications also. There is preferably a gas exchanger between the arteries and the pump, which oxygenates the blood and removes carbon dioxide from the blood. Typically there is heat exchanger, which keeps the blood at a temperature close to normal body temperature. Preferably, the heat exchanger is integrated with either the gas exchanger or the pumping chamber. This decreases the possibility of formation of air bubbles, since the solubility of gas changes when temperature changes.

There are preferably one way valves between the pump and veins or arteries, which allow the blood to flow only from the veins to the pump and from the pump to the arteries. Furthermore, there is usually a mechanism or mechanisms to control circulation volume through the pump as needed.

Additionally, there is usually a mechanism for coordinating the pumping activity with heart contraction if heart contraction occurs or whenever this coordination is needed. Arterial pressure or EKO information may be used for this coordinating purpose. For example, a pressure sensor may be integrated into the arterial catheter, which delivers blood to the artery, or a separate arterial pressure sensor may be used to measure arterial pressure. This pressure signal feeds back to the pump for controlling the rate of the pump for maintaining the arterial pressure at a preset level.

The QRS complex of the EKG and arterial pressure from the patient can be used to coordinate pump activity with contraction of the heart. There is preferably coordination between the EKG gating and pressure control of the pump activity. The QRS complex stops the pump, and a fall in arterial pressure detected by the pressure control system of the pump resumes the pump activity. This design assures that the heart does not contract against the pump and that pump activity starts right after the heart completes its contraction. In this manner, the pump will work in coordination with the heart to avoid stress from the pump working against the heart and to facilitate induction and maintenance of the asystolic or nearly asystolic status and resumption of the normal activity of the heart when desired.

If arterial pressure is below a preset value, the pressure control will override the EKG gating to assure adequate perfusion pressure to the organs. During asystolic or nearly asystolic status, the pump is controlled by an intrinsic pumping rate or volume to maintain blood pressure within a present range. EKG gating and the pressure control mechanism continue to work to avoid the heart contracting against the pump. Appropriate pressure ranges are well known in the art. The preset pressure is selected to maintain adequate perfusion to the vital organs. For example, a mean arterial pressure of about 60 to 90 mm Mercury is usually thought to be appropriate.

A pressure sensor can also be used to measure central venous pressure. If central venous pressure is too high, such as higher than 18 mmHg, the pump rate or the pumping volume or both is increased for draining the venous blood and, therefore, decreases the central venous pressure to an optimal level, such as 12 mmHg. This may be particularly important when myocardial infarction involves the right ventricle. In this situation, an increase in central venous pressure may cause increased pressure of the right ventricle. This increases oxygen consumption of the right ventricle and decreases blood supply to the right ventricle and, therefore, can cause further damage to the right ventricle or prevent or compromise the recovery of the cardiac muscle from the insult. This central venous pressure control means works in conjunction with an arterial pressure control and an EKG gating means and preferably works when the arterial pressure control and EKG gating are fully operational.

In a preferred embodiment, the pump includes two pumping chambers that are mechanically compressible and extendible. These two chambers work in a coordinated manner, meaning that while one is filling, the other is draining. This double chamber design provides an advantage in that the pump pumps the blood into the artery and drains the blood from the vein whenever the pump is reset by a QRS complex. For example, when a QRS complex resets the pump with one chamber in the pumping status and the other in draining status, the pump will restart with the pumping chamber pumping and draining chamber draining.

Alternatively, the pump can be adapted to sense which chamber contains more blood volume, and reset itself such that a chamber with more blood is in a pumping status and the other is in a draining status. Without this design, when a single chamber is reset by a QRS complex at the end of its pumping status, it will be less able to pump blood into the artery and, therefore, will be less able to maintain the blood pressure effectively. This is even more important when the heart rate is relatively fast. A single chamber pump would not have enough time to coordinate with spontaneous heart contractions, which would result in ineffective pump activity and decrease in blood pressure. It would cause hypoperfusion of the organs including the heart and brain. Damage to the organ could occur.

This preferred design more effectively maintains arterial pressure and unloads the right ventricle and, therefore, the left ventricle since, if the right ventricle is loaded, it will pump the blood to the left ventricle in a following cardiac cycle. This preferred design also allows a relatively long pumping and draining cycle of each chamber without compromise of blood circulation since the two chambers work in a coordinated fashion.

In a preferred embodiment, the pumping phase of each chamber is shorter than the draining phase with the gas exchanger located between the vein and the chambers. This generates a pulsatile pressure to mimic physiological blood pressure, which is important to enhance perfusion to the heart and other organs. It allows a relatively longer time for blood to flow through the gas exchanger at lower speed. This permits better oxygenation with a smaller exchanger and less sheering force. This in turn makes it possible to decrease blood volume circulating in the pumping system and cause less hemolysis and less coagulation abnormality due to less sheering force.

The chambers are connected to the venous and arterial catheters. The chamber volume is adjustable as needed. For example, when heart rate is faster, chamber volume may decrease with an increase in the pumping rate. Both the venous and arterial catheters contain one-way valves, which only allow blood to flow from the vein to the pump and from the pump to artery. When a chamber is expanded, a negative pressure is created in the chamber, which draws blood from the vein. When a chamber is compressed, a positive pressure is created which pumps the blood into the artery through the arterial catheter. These actions create a pulsatile pressure, which can avoid side effects of non-pulsatile pressure on the perfusion of the organs of the human body. It is known that non-pulsatile pressure may be harmful to the organs.

Selection of pump rates and chamber volumes are well within the skill of the ordinary practitioner of the invention.

Pump rate is usually selected from a range of about 30 to 100 contractions per minute. More preferably, the range is from 50 to 85 beats per minute. The practitioner is aware of the interrelationship between pump rate and pump volume. For instance, a faster pump rate would be expected to correlate with a somewhat lower chamber volume, whereas a larger chamber volume would be expected to accommodate a somewhat lower pump rate. Usually, in an adult patient, the chamber would contain about 60 to 100 milliliters of blood volume. Pediatricians are well aware of the different volume and pressure requirements for their patients, and would adjust the parameters accordingly.

The venous draining catheter preferably enters the chamber from the top of the chamber to allow possible air bubbles to accumulate in a cone shaped top space where they can be readily removed. The arterial catheter is typically located at bottom of the chamber to decrease the possibility of air bubbles entering the arterial system, which may cause air embolism. The coordination between the two chambers can be disengaged when necessary to stop one pump for any reason, such as to remove air bubbles accumulated in the chamber. This coordination can be re-engaged as well. Typically the chamber contains priming solution for filling up the system and purging air bubbles to establish cardiopulmonary bypass circulation, such as normal saline.

The following additional preferred embodiments refer to the figures for illustrative purposes. FIG. 1 is a diagram of the pump system. Number 2 is a catheter which drains blood from the vein of a patient to a pump and contains a one way valve only allowing the blood to flow from the patient to the pump. Number 4 is a pump which creates a negative pressure to drain blood from the vein and positive pressure to pump the blood through a gas exchanger and back to the artery of the patient. Number 6 is a catheter which connects the pump to the gas exchanger or a heat exchanger or both (8) and then to the body of the patient. The blood from the vein is pumped back to the artery of the patient through this catheter which also contains a pressure sensor (9), which senses an arterial pressure of the patient and feeds back this information to the pump to maintain a preset arterial pressure. Number 8 is a commercially available gas and heat exchanger combination, which removes carbon dioxide and oxygenates the blood and keeps the temperature of the blood at similar level to the body temperature of the patient. Number 10 is an EKG unit located in the pump or connected to the pump and is used to gate the pump activity. It may stop the pump if an EKG signal, such as a QRS complex, is sensed. It may be bypassed on the choice of a physician or overridden by a pressure control function of the pump.

Figure 2:
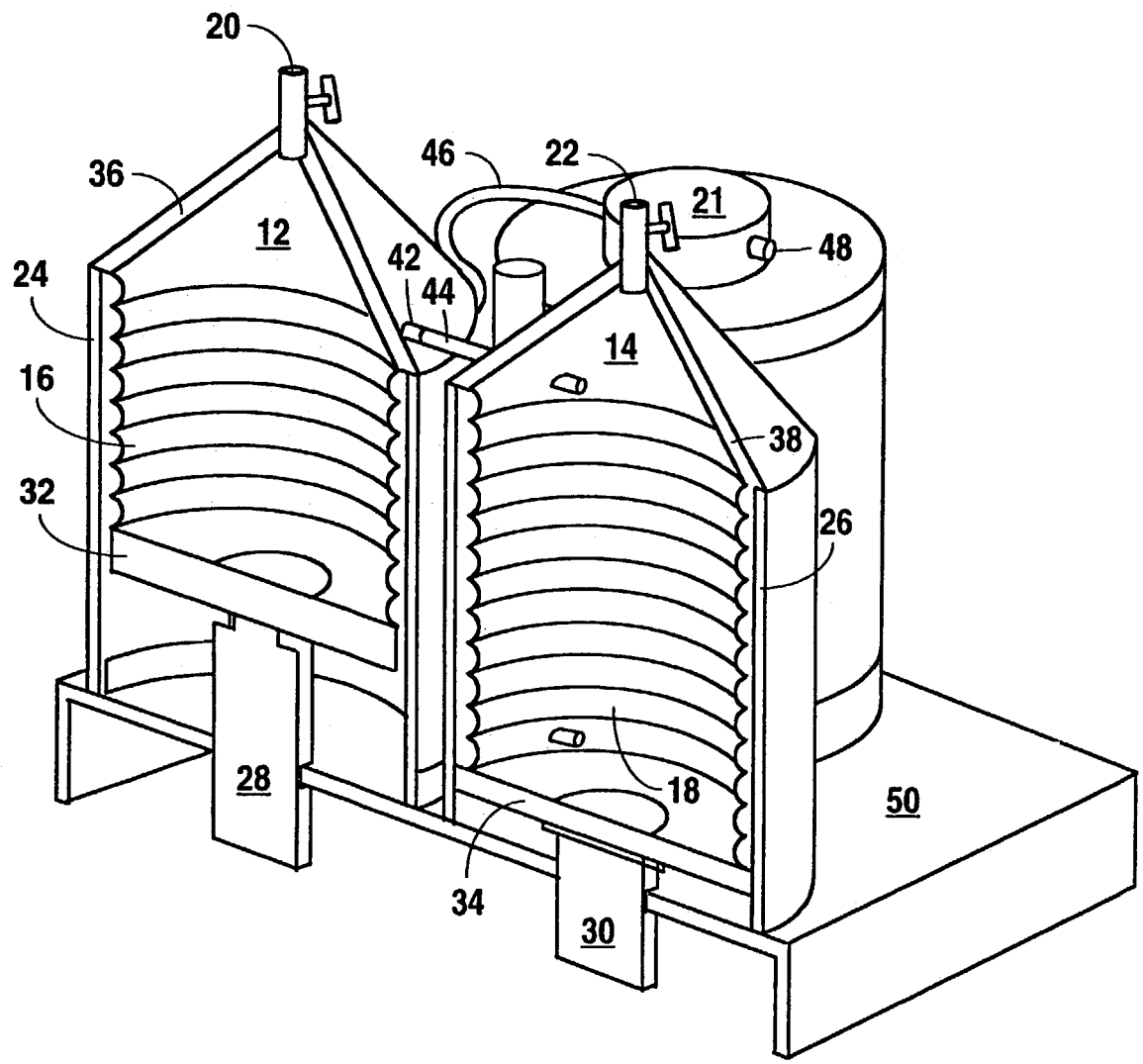
FIG. 2 is a sectional view of the pumping chambers of a preferred embodiment.

FIG. 2 is a sectional view of the pumping chambers. Number 12 is a solid and non-expandable portion of a pumping chamber. Number 14 is a solid and non-expandable portion of a pumping chamber, which is equivalent in function and similar to the chamber numbered 12. Air can accumulate in the top portion of the cone shaped space for removal. Number 16 is an expandable portion of the pumping chambers. When it is expanded, a negative pressure is created in the chamber and blood is drained into the chamber. When it is compressed, a positive pressure in the chamber pumps the blood into the artery of the patient through a gas exchanger. Number 18 is an expandable portion of the other pumping chamber equivalent to that described as number 16. Number 20 and 22 are stopcocks for each corresponding chamber for removing air bubbles accumulated in the chambers. Numbers 24 and 26 are solid cylinders to protect each corresponding pumping chamber. Numbers 28 and 30 are solid rods connecting a driving mechanism to the bottom portion of the respective pumping chambers for compressing and expanding the chambers. Numbers 32 and 34 are solid bottom portions of the pumping chambers. Numbers 36 and 38 are solid cone shaped top portions of each corresponding pumping chamber. Numbers 42, 44 and 46 are tubings connecting the gas exchanger to the pumping chambers and containing one way valves, which allow the blood to flow only from the gas exchanger to the pumping chambers. Number 21 is a gas exchanger, which is used to oxygenate the blood and to remove carbon dioxide from the blood. Number 48 is an inlet receiving the blood from a patient. Number 50 is a base of the pump, which contains pump machinery and control mechanisms.

Figure 3:
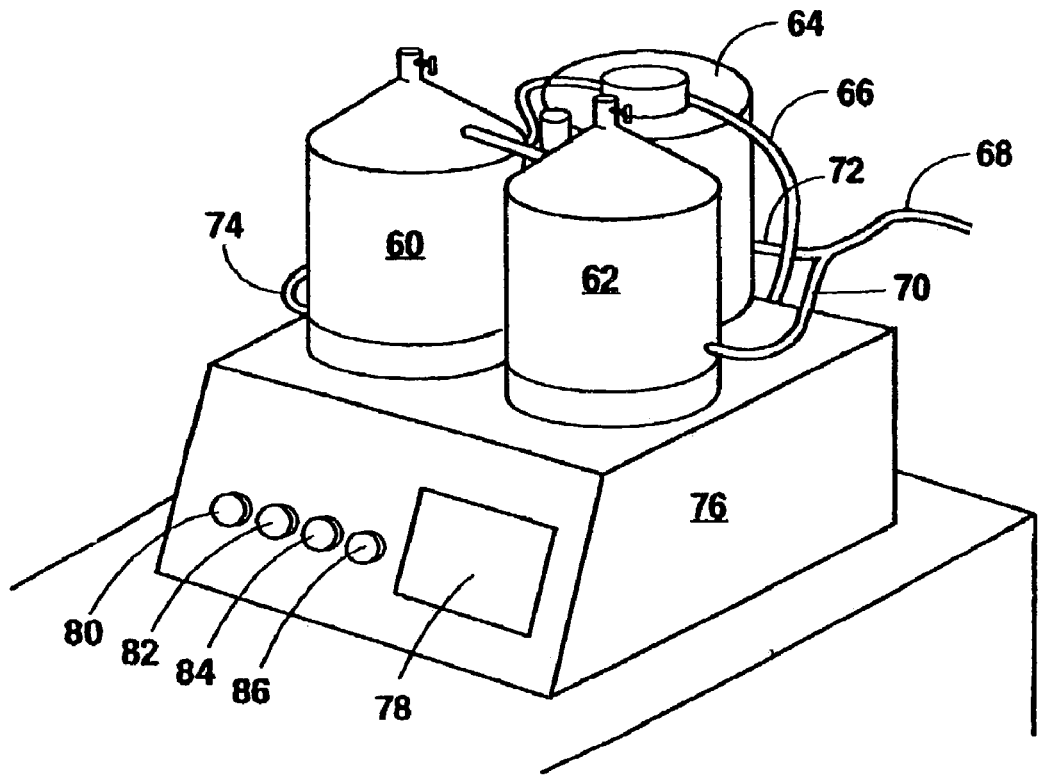
FIG. 3 is a view of a pump of the invention.

FIG. 3 is a drawing of the pump. Numbers 60 and 62 are two equivalent pumping chambers. Number 64 is a gas exchanger. Number 66 is a tubing draining the blood from a patient to the gas exchanger. Number 68 is tubing for delivering blood from the pumping chambers to the patient. Numbers 72 and 70 are tubings which connect the corresponding pumping chamber to number 68. Each tubing contains a one way valve allowing blood to flow only from the corresponding pumping chamber to the patient, or from the patient to the appropriate chamber. Number 74 is a continuation of the tubing numbered as 72. Number 76 is the base of the pump. Number 78 is a screen showing EKG and blood pressure tracings. Numbers 80, 82, 84 and 86 are switches for control of the pump, such as EKG gating and pressure control engagement and disengagement of the two pumping chambers.

EXAMPLE

When a patient needing cardiac rest or cardiopulmonary circulation is identified, venous and arterial catheters are inserted with standard procedure in a major vein and artery, such as the femoral vein and artery or the jugular vein and/or axillary arteries. The venous and arterial catheters are connected to the cardiopulmonary bypass machine. After reliable bypass circulation is established, medication, such as esmolol (a beta adrenergic blocker) or diltiazem (a calcium channel blocker) or both, if needed, are infused into patient's vein in an incremental manner to allow the heart rate to gradually decrease over a short period of time such as 15 minutes.

If control of the heart rate is not adequate, potassium may be used to create a hyperkalemic status and a severe bradycardia or asystolic status. When ventricular tachycardia or fibrillation occurs, large doses of antiarrhythmics, such as Quinidine and Procainaminde, may be used to stop these rhythm disturbances without the usual consequences of asystole caused by the medication. These medications can be used to induce asystolic or nearly asystolic status.

The bypass machine is activated when the arterial pressure is below a pre-.set level, such as 60 mm Hg mean arterial pressure. The EKG gating and pressure control mechanisms are activated and functions in the previously described manner to avoid the heart contracting against the machine. Eventually, heart rate decreases to a few beat per minutes. Hemostasis in the pulmonary circulation is avoided by letting the heart contract a few times per minute. Pump rate or pumping volume or both are controlled by pressure feedback from the artery to maintain the blood pressure at a preset level. The patient's blood circulation may be maintained in this manner for hours to days depending on the clinical condition of the patient.

When the patient is ready to be weaned off the machine, infusion of the medication is decreased in a decremental manner with the pump operating under pressure control and EKO gating mechanisms. This maintains adequate perfusion of the organs and avoids the heart contracting against pressure generated by the pump. This also allows a cardiologist to perform procedures such as angioplasty and coronary stenting to the left main coronary artery or to severely stenotic coronary, arteries or both.

The heart may be put into asystole for a period of time to allow certain procedures to be performed such as minimally invasive bypass surgery or some catheter based intervention, such as angioplasty and stenting to the coronary arteries. Previously, such patients were thought to be unsuitable or at extremely high risk for angioplasty and required bypass surgery, since failure of angioplasty to open these vessels presents an immediate risk for massive heart attack or death. With the pump replacing the function of the heart and the heart in an asystolic status, angioplasty and stenting or minimal bypass surgery to these vessels can be done and the result can be monitored with minimal risk of massive heart attack or death if the procedure fails, since the function of the heart is replaced by the pump and the work load on the heart is extremely low.

The pump is also can be used for respiratory failure, which will provide reliable oxygenation of the blood and avoid intubation of the trachea.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications can be practiced within the scope of the appended claims.

The invention claimed is:

1. A method of facilitating cardiac rest in a human comprising:
    inducing a controlled asystolic state in the human and applying life support techniques while the human is in the asystolic state, the life support techniques comprising application of a closed extra-corporeal circulation system having:
    (a) a venous conduit,
    (b) a gas exchanger,
    (c) a pump for pumping at least a portion of the human's blood,
    (d) arterial conduit, and
    (e) EKG gating mechanism comprising an EKG sensor means for sensing the human's heartbeat, and a feedback means for coordinating the EKG sensor means with the pump wherein the pump discontinues for a time of at least one heartbeat sensed by the EKG sensor means and resumes pumping when the heartbeat is not sensed by the EKG sensor means, wherein said pumping provides a rate or a volume sufficient to maintain blood pressure above a preset level and is controlled by an intrinsic rate and/or volume setting,
    wherein said circulation system is arranged such that the venous conduit is connected to a vein of the patient, the arterial conduit is connected to an artery of the patient, the gas exchanger is connected to at least one of the venous conduit and the arterial conduit, and the pump is connected to at least one of the venous conduit and the arterial conduit, and
    wherein the gas exchanger is adapted to remove at least a portion of a quantity of carbon dioxide from the patient's blood and is further adapted to add a quantity of oxygen to the patient's blood.

2. The method of claim 1 wherein the induction includes administration of a medication selected from a group comprising calcium channel blockers, beta adrenergic blockers, antiarrhythmic agents and potassium.

3. The method of claim 1 wherein the pump is a pulsatile pump.

4. The method of claim 1 wherein the closed system includes an arterial pressure sensor, said pressure sensor having a feedback means for coordinating the arterial pressure of the human with the pumping of the pump such that the pump changes at least one of pumping rate and pumping volume when the pressure sensor senses a pressure different from a predetermined arterial pressure range, and wherein the pressure sensor re-initiates the pumping after EKG gating means stops the pumping activity and when the blood pressure to sensor senses a fall in blood pressure below the preset level.

5. A method of claim 4 wherein the pump increases a volume output of the pump by changing at least one of pump rate and pump volume when the pressure sensor senses an arterial pressure less than the preset arterial pressure level and decreases a pumping rate when the pressure sensor senses an arterial pressure higher than the preset arterial pressure level.

6. The method of claim 5 wherein the pump includes at least two chambers.

7. The method of claim 6 wherein a two chambered pump is coordinated such that one of the chambers is receiving blood into itself while the other of the chambers is emptying blood from itself.

8. The method of claim 7 wherein the closed system further includes a QRS reset mechanism, said mechanism adapted to (a) sense a QRS complex generated by the patient and to (b) reset the pump's pumping when the QRS complex is sensed by the reset mechanism, wherein the resetting of the pumping is accomplished such that the chamber that was receiving blood before the reset will resume receiving blood until a predetermined volume is received, and such that the chamber emptying blood will resume emptying blood until a predetermined volume is emptied.

9. The method of claim 4 wherein the closed system includes a gating coordination means for coordinating the EKG sensor means with the arterial pressure sensor means.

10. The method of claim 9 to promote adequate arterial blood pressure in the human wherein the pressure sensor means is adapted to override the EKG gating means to control the pump for at least one of pumping rate and pumping volume.

11. The method of claim 1 further including a heat exchanger connected with any two of the group comprising the arterial conduit, the pump, the gas exchanger, and the venous conduit.

12. A method of facilitating cardiac rest in a patient comprising:
    inducing a controlled reversible brachycardia or reversible asystole in the patient and applying life support techniques while the patient is in the asystolic state, the life support techniques comprising application of a closed extra-corporeal circulation system having:
    (a) a venous conduit,
    (b) a gas exchanger,
    (c) a pump for pumping at least a portion of the patient's blood, (d) arterial conduit, and (e) EKG gating mechanism comprising an EKG sensor means for sensing the patient's heartbeat, and a feedback means for coordinating the EKG sensor means with the pump wherein the pump discontinues for a time of at least one heartbeat sensed by the EKG sensor means and resumes pumping when the heartbeat is not sensed by the EKG sensor means, wherein said pumping provides a rate or a volume sufficient to maintain blood pressure above a preset level and is controlled by an intrinsic rate and/or volume setting, wherein said circulation system is arranged such that the venous conduit is connected to a vein of the patient, the arterial conduit is connected to an artery of the patient, the gas exchanger is connected to at least one of the venous conduit and the arterial conduit, and the pump is connected to at least one of the venous conduit and the arterial conduit, and wherein the gas exchanger is adapted to remove at least a portion of a quantity of carbon dioxide from the patient's blood and is further adapted to add a quantity of oxygen to the patient's blood.

13. The method of claim 12 wherein the bradycardia is from 1 to 60 beats per minute.

14. The method of claim 12 wherein the bradycardia is from 1 to 10 beats per minute.

15. A method of facilitating cardiac rest in a patient who has sustained a cardiac insult comprising:

(a) induction of a controlled state of lowered metabolism of the myocardium of the human, said state including decreased heart rate and decreased oxygen utilization; and (b) administration of life support techniques including extra-corporeal circulation through a closed system, said system having a pump, a gas exchanger, a heat exchanger, a systolic gating mechanism and EKG gating mechanism that comprises an EKG sensor means for sensing the human's heartbeat, and a feedback means for coordinating the EKG sensor means with the pump wherein the pump discontinues for a time of at least one heartbeat sensed by the EKG sensor means and resumes pumping when the heartbeat is not sensed by the EKG sensor means, wherein said pumping provides a rate or a volume sufficient to maintain blood pressure above a preset level and is controlled by an intrinsic rate and/or volume setting, and wherein said controlled state of lowered metabolism facilitates further treatment to the heart without injury to the heart or compromise of blood supply the other vital organs.

16. The method of claim 15 wherein said gas exchanger is adapted to remove CO2 from and to add 02 to at least a portion of a volume of blood pumped through the closed system; and further wherein said gas exchanger is located in series between a vein of the human and the pump.

\* \* \* \* \*